Figure 4:
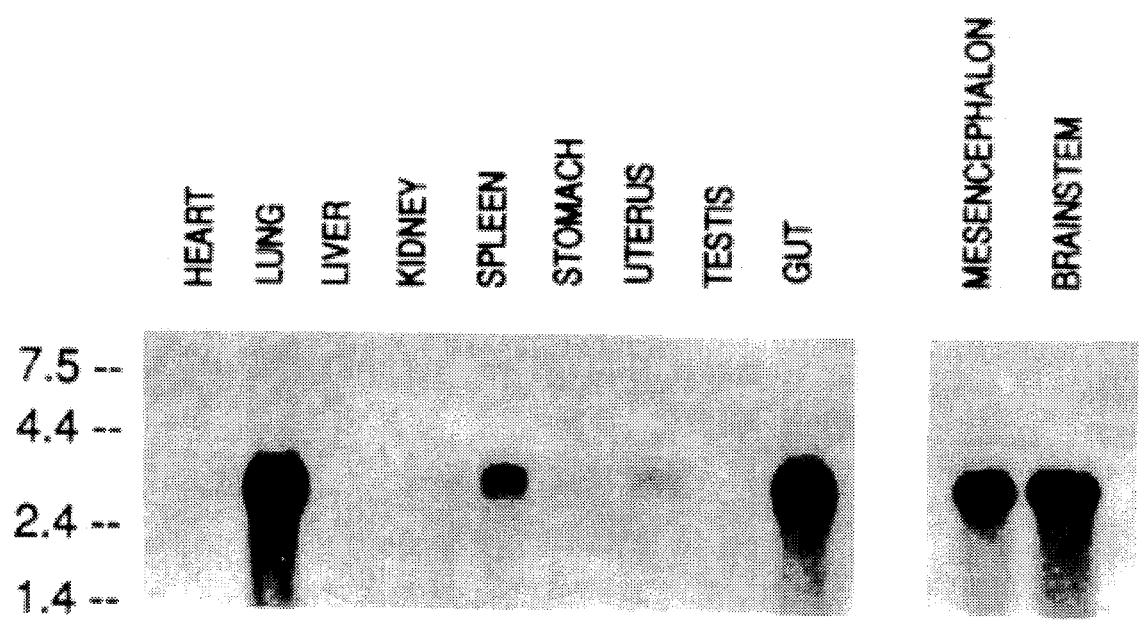

United States Patent [19]

Hoffman et al.

[11] Patent Number: 5,552,308
[45] Date of Patent: Sep. 3, 1996

[54] CDNA CLONE OF A RAT SEROTONIN TRANSPORTER AND PROTEIN ENCODED THEREBY

[75] Inventors: Beth J. Hoffman, Kensington; Eva Mezey; Michael J. Brownstein, both of Rockville, all of Md.

[73] Assignee: The United States of America as represented by the Department of Health and Human Services, Washington, D.C.

[21] Appl. No.: 782,298

[22] Filed: Oct. 24, 1991

[51] Int. Cl.$^6$ ................................................. C12N 15/12
[52] U.S. Cl. ............... 435/172.3; 435/69.1; 435/252.3; 435/320.1; 536/23.5
[58] Field of Search ................................ 435/69.1, 252.3, 435/320.1; 536/27

[56] References Cited

U.S. PATENT DOCUMENTS 4,675,285  7/1987  Clark et al. .................................. 435/6

FOREIGN PATENT DOCUMENTS 9006047  7/1990  WIPO .

OTHER PUBLICATIONS

Dr. D. S. 85: 9846–9850 (Dec. 1988) Blakely et al. Expression of Neurotransmitter transport from rat brain mRNA in *Xenopus laevis* oocytes Nature 330: 379–381 (26 Nov. 1987) Hediger et al Expression cloning and cDNA sequencing of the Na$^+$/glucose co-transporter.

Biochemistry 29:3349–3354, 1990, Jul., Biessen et al. Parts of Purification of the 5–Hydroxytryptamine Reuptake System from Human Blood Platelets . . . .

Pletscher, International Journal of Cardiology, 14 (1987) 177–188, The 5–hydroxytryptamine system of blood platlets: physiology and pathophysiology.

Nelson et al, FEBS 08757, vol. 269, No. 1, 181–184 Cloning of the human brain GABA transporter.

Guastella, et al, Science, Sep. 14, 1990, 1303–1306, vol. 249 Cloning and Expression of a Rat brain GABA Transporter.

Pacholszyk et al, Nature, vol. 350, Mar. 28, 1991, 350–354, Expression cloning of a cocaine–and antidepressant–sensitive human noradrenaline transporter.

*Primary Examiner*—Garnette D. Draper
*Assistant Examiner*—John D. Ulm
*Attorney, Agent, or Firm*—Birch, Stewart, Kolasch & Birch, LLP

[57] ABSTRACT

The invention described in this disclosure relates to a cloned cDNA encoding the serotonin transporter protein (5HTT) usually found in cells of part of the central nervous system, gut, adrenal gland and in platelets. The invention is further directed to the purified serotonin transporter protein and its use and immunogen for the production of anti-5HTT antibodies. The disclosure also discussses methods for use of the cDNA for diagnostic and treatment applications, and methods for use of permanent cell lines transformed with the serotonin transporter cDNA for pharmaceutical screening. The use of anti-5HTT antibodies as a diagnostic tool is also addressed.

5 Claims, 7 Drawing Sheets

5'-TAGGGGATCAGGAAGGCGCCGCCCNCCRTTYTTNYMRCACAGGTAGGGAAGCCACACATT-3'

FIGURE 1

```
  1  METTPLNSQK VLSECKDRED CQENGVLQKG VPTTADRAEP SQISNGYSAV

51  PSTSAGDEAS HSIPAATTTL VAEIRQGERE TWGKKMDFLL SVIGYAVDLG

101  NIWRFPYICY QNGGAFLLP YTIMAIFGGI PLFYMELALG QYHRNGCISI

151  WRKICPIFKG IGYAICIIAF YIASYYNTII AWALYYLISS LTDRLPWTSC

201  TNSWNTGNCT NYFAQDNITW TLHSTSPAEE FYLRHVLQIH QSKGLQDLGT

251  ISWQLTLCIV LIFTVIYFSI WKGVKTSGKV VWVTATFPYI VLSVLLVRGA

301  TLPGAWRGVV FYLKPNWQKL LETGVWVDAA AQIFFSLGPG FGVLLAFASY

351  NKFNNNCYQD ALVTSVVNCM TSFVSGFVIF TVLGYMAEMR NEDVSEVAKD

401  AGPSLLFITY AEAIGNMPAS TFFAIIFFLM LITLGIDSTF AGLEGVITAV

451  LDEFPHIWAK RREWFVLIVV ITCVLGSLLT LTSGGAYVVT LLEEYATGPA

501  VLTVALIEAV AVSWFYGITQ FCSDVKEMLG FSGMVWRICW VAISPLFLLF

551  IICSFLMSPP QLRLFQYNYP HWSIVLGYCI GMSSVICIPT YIIYRLISTP

601  GTLKERIIKS ITPETPTEIR VGHPHECCVT HPGRGHLFPA TSLSSEKPTG

651  LLL
```

FIGURE 2

FIG. 3A
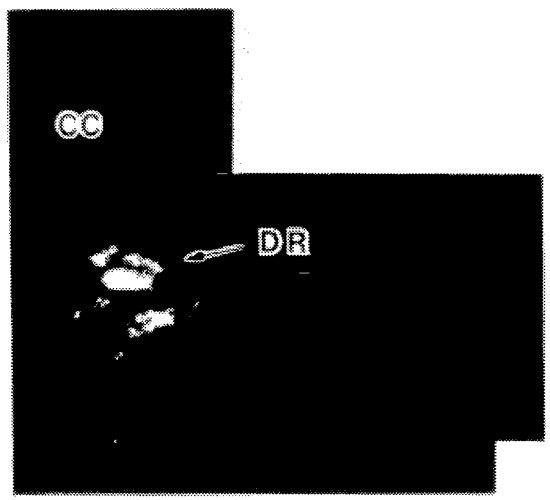
FIG. 3B
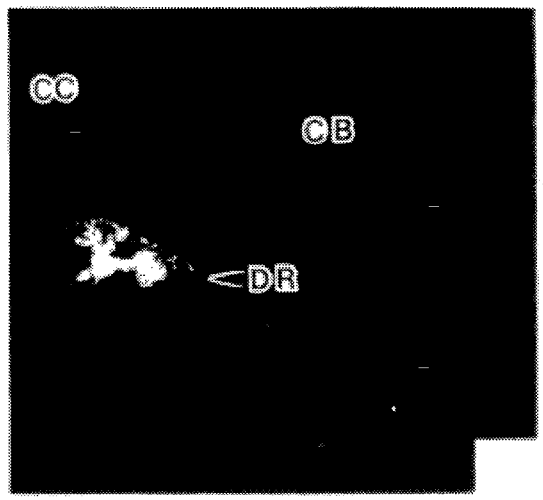
FIG. 3C
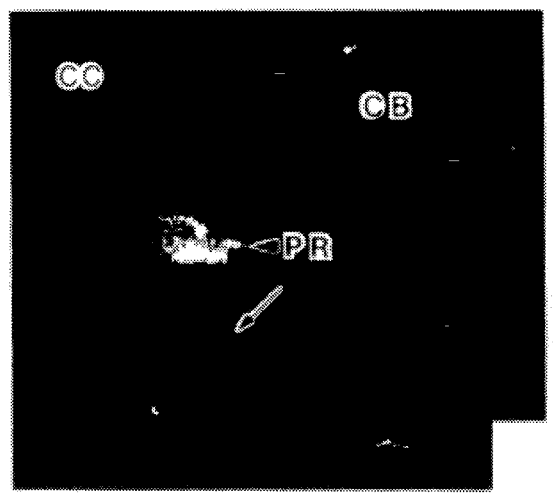
FIG. 3D
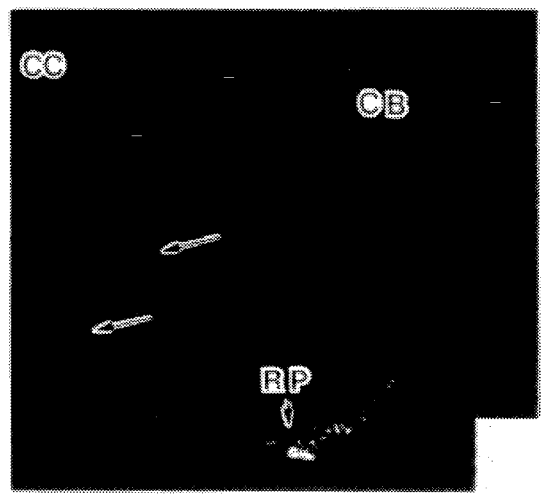
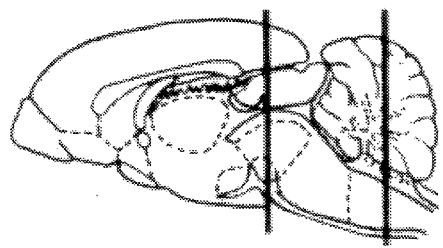
FIG. 3E 5-HT transporter cDNA sequence:

```
   1  CGCGCCGGTG CCTCGAGGGC GCGAGGGTCG CGCCGCCTCC GCAGCCCGGG
  51  ACCCGCCGCC GCGCCGCCCG CAGAACTTGG CAGCAGTTCC CACCCAACCC
 101  CTGCTGGACT TAAGGGACAT ACTAGAGCTT TCCGTCTTGT CCCCATAACC
 151  CGAGAGGAGA TCAAACCAAG AACCAAGAGC TAGCCTGGGT CCTCGGCAGA
 201  TGGGAATCCG CATCACTTAC TGACCAGCAG CATGGAGACC ACACCCTTGA
 251  ATTCTCAGAA AGTGCTGTCA GAGTGTAAGG ACAGAGAGGA CTGTCAAGAA
 301  AATGGTGTTC TACAGAAGGG TGTCCCCACC ACAGCGGACA GGGCAGAGCC
 351  TAGCCAAATA TCCAATGGGT ACTCTGCAGT CCCCAGCACA AGTGCAGGGG
 401  ACGAAGCTTC ACACTCGATC CCAGCTGCCA CCACCACCCT GGTGGCTGAG
 451  ATTCGCCAAG GGGAGCGGGA GACCTGGGGC AAGAAGATGG ATTTCCTCCT
 501  GTCCGTCATT GGCTATGCCG TGGACCTGGG CAACATCTGG CGGTTTCCTT
 551  ACATATGCTA CCAGAATGGC GGAGGGGCCT TCCTCCTCCC TTATACCATC
 601  ATGGCCATTT TCGGGGGGAT CCCGCTCTTT TACATGGAGC TCGCACTGGG
 651  CCAGTACCAC CGAAACGGGT GCATTTCCAT ATGGAGGAAG ATCTGCCCGA
 701  TTTTCAAAGG CATTGGTTAC GCCATCTGCA TCATCGCCTT TTACATCGCC
 751  TCCTACTACA ACACCATCAT AGCCTGGGCG CTCTACTACC TCATCTCCTC
 801  CCTCACGGAC CGGCTGCCCT GGACCAGCTG CACGAACTCC TGGAACACTG
 851  GCAACTGCAC CAACTACTTC GCCCAGGACA ACATCACCTG GACGCTGCAT
 901  TCCACGTCCC CCGCTGAGGA GTTCTACTTG CGCCATGTCC TGCAGATCCA
 951  CCAGTCTAAG GGACTCCAGG ACCTGGGCAC CATCAGCTGG CAGCTGACTC
1001  TCTGCATCGT GCTCATCTTC ACCGTAATCT ACTTTAGCAT CTGGAAAGGC
1051  GTCAAAACAT CTGGCAAGGT GGTGTGGGTG ACAGCCACCT TCCCATACAT
1101  TGTCCTCTCT GTCCTGCTGG TGAGGGGGGC CACCCTTCCT GGAGCCTGGA
1151  GAGGGGTCGT CTTCTACTTG AAACCCAACT GGCAGAAACT CTTGGAGACA
1201  GGGGTGTGGG TAGATGCCGC CGCTCAGATC TTCTTCTCTC TTGGCCCGGG
1251  CTTTGGGGTT CTCCTGGCTT TTGCTAGCTA CAACAAGTTC AACAACAACT
```

FIGURE 5A

```
1301  GTTACCAAGA TGCCCTGGTG ACCAGTGTGG TGAACTGCAT GACAAGCTTC
1351  GTCTCTGGCT TCGTCATCTT CACGGTGCTT GGCTACATGG CGGAGATGAG
1401  GAATGAAGAT GTGTCAGAGG TGGCCAAAGA CGCAGGCCCC AGCCTCCTCT
1451  TCATCACGTA TGCAGAGGCA ATAGGCAACA TGCCAGCATC CACGTTCTTT
1501  GCCATCATCT TCTTCCTCAT GTTAATCACG CTGGGATTGG ACAGCACGTT
1551  CGCAGGCCTG GAAGGTGTGA TCACAGCTGT GCTGGATGAG TTCCCTCACA
1601  TCTGGGCCAA GCGCAGGGAA TGGTTCGTGC TCATCGTGGT CATCACGTGC
1651  GTCTTGGGAT CCCTGCTCAC ACTGACGTCA GGAGGGCAT ACGTGGTGAC
1701  TCTGCTGGAG GAGTATGCCA CGGGGCCAGC AGTGCTCACC GTGGCCCTCA
1751  TCGAGGCCGT CGCCGTGTCT TGGTTCTATG GAATCACTCA GTTCTGCAGC
1801  GATGTGAAGG AGATGCTGGG CTTCAGCGGG ATGGTTTGGA GGATCTGCTG
1851  GGTGGCCATC AGCCCTCTGT TTCTCCTGTT CATCATTTGC AGTTTTCTGA
1901  TGAGCCCACC CCAGCTACGG CTTTTCCAAT ACAACTATCC CCACTGGAGT
1951  ATCGTCTTGG GCTACTGCAT AGGGATGTCG TCCGTCATCT GCATCCCTAC
2001  CTATATCATT TATCGGCTGA TCAGCACTCC GGGGACACTT AAGGAGCGGA
2051  TTATTAAAAG TATCACTCCT GAAACACCCA CAGAAATCCG TGTGGGACAT
2101  CCGCATGAAT GCTGTGTAAC ACACCCTGGG AGAGGACACC TCTTCCCAGC
2151  CACCTCTCTC AGCTCTGAAA AGCCCACTGG ACTCCTCCTC TAAGCAAGCT
2201  GATGAAGACA CGTCTAACAC TATGTGCCAG ACTCTGTGGA TCCGACCACT
2251  TCTTTCCGTG GACTCTCAGA CATGCTACCA CATTCGATGG TGACACCACT
2301  GAGCTGGCCT CTTGGACACG TCAGGGAGTG GAAGGAGGGA TGAACGCCAC
2351  CCAGTCATTC AGCTAGCTTC AGTTTAGAAT TAGGTCTGTG AGAGTCTGTT
2401  ACTAGTTTTT GGTAAGTACT AACTACCCCG CATCTGTTAG CTTCTAAAGC
2451  CTTCAATGTT CATGAATACA TAAACCACCT AAGAGAAAAC ATATATGTCT
2501  TGCTAGCCAT ATATATTTTC TCGGTAGCAT AGAATTCTAT AGCTGGAATC
2551  TCCTAGAACC CTGTAACCCA CGTGCTGCTG TGAGGTTAAG GAGGGAAGGT
2601  GTAAGGATTG CTACACTGAA AAAATGGTGT ATATGTGTGA GCTATTGTGT
```

FIGURE 5B

2651 CTGTCCATTA TCGTCTGTGA GCCCTCGATC CCAATACTCC AGGTCCATTT

2701 CAAACTGTAT AAATGGCCTC TAATTTTTCT TACATTAAAC AGATTCTACC

2751 TAAAAA

FIGURE 5C

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2756 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Rattus rattus
        ( G ) CELL TYPE: Mast Cell
        ( H ) CELL LINE: RBL 2H3

( i x ) FEATURE:
        ( A ) NAME/KEY: CDS
        ( B ) LOCATION: 232..2190
        ( D ) OTHER INFORMATION: /function="serotonin uptake"
            / product="serotonin transporter"
            / standard_name="5HTT"

( x i ) SEQUENCE DESCRIPTION: SEQ ID NO:1:

```
CGCGCCGGTG  CCTCGAGGGC  GCGAGGGTCG  CGCCGCCTCC  GCAGCCCGGG  ACCCGCCGCC           60

GCGCCGCCCG  CAGAACTTGG  CAGCAGTTCC  CACCCAACCC  CTGCTGGACT  TAAGGGACAT          120

ACTAGAGCTT  TCCGTCTTGT  CCCCATAACC  CGAGAGGAGA  TCAAACCAAG  AACCAAGAGC          180

TAGCCTGGGT  CCTCGGCAGA  TGGGAATCCG  CATCACTTAC  TGACCAGCAG  C  ATG  GAG         237
                                                              Met  Glu
                                                               1

ACC  ACA  CCC  TTG  AAT  TCT  CAG  AAA  GTG  CTG  TCA  GAG  TGT  AAG  GAC  AGA   285
Thr  Thr  Pro  Leu  Asn  Ser  Gln  Lys  Val  Leu  Ser  Glu  Cys  Lys  Asp  Arg
          5                        10                       15

GAG  GAC  TGT  CAA  GAA  AAT  GGT  GTT  CTA  CAG  AAG  GGT  GTC  CCC  ACC  ACA   333
Glu  Asp  Cys  Gln  Glu  Asn  Gly  Val  Leu  Gln  Lys  Gly  Val  Pro  Thr  Thr
         20                        25                       30

GCG  GAC  AGG  GCA  GAG  CCT  AGC  CAA  ATA  TCC  AAT  GGG  TAC  TCT  GCA  GTC   381
Ala  Asp  Arg  Ala  Glu  Pro  Ser  Gln  Ile  Ser  Asn  Gly  Tyr  Ser  Ala  Val
 35                       40                       45                      50

CCC  AGC  ACA  AGT  GCA  GGG  GAC  GAA  GCT  TCA  CAC  TCG  ATC  CCA  GCT  GCC   429
Pro  Ser  Thr  Ser  Ala  Gly  Asp  Glu  Ala  Ser  His  Ser  Ile  Pro  Ala  Ala
```

|  |  |  |  |  |  |  |  |  |  |  |  |  |  |  |  |
|---|---|---|---|---|---|---|---|---|---|---|---|---|---|---|---|
|  |  |  |  | 55 |  |  |  |  | 60 |  |  |  |  | 65 |  |
| ACC | ACC | ACC | CTG | GTG | GCT | GAG | ATT | CGC | CAA | GGG | GAG | CGG | GAG | ACC | TGG |
| Thr | Thr | Thr | Leu | Val | Ala | Glu | Ile | Arg | Gln | Gly | Glu | Arg | Glu | Thr | Trp |
|  |  |  | 70 |  |  |  |  | 75 |  |  |  |  | 80 |  |  |

477

| GGC | AAG | AAG | ATG | GAT | TTC | CTC | CTG | TCC | GTC | ATT | GGC | TAT | GCC | GTG | GAC |
|---|---|---|---|---|---|---|---|---|---|---|---|---|---|---|---|
| Gly | Lys | Lys | Met | Asp | Phe | Leu | Leu | Ser | Val | Ile | Gly | Tyr | Ala | Val | Asp |
|  |  | 85 |  |  |  |  | 90 |  |  |  |  | 95 |  |  |  |

525

| CTG | GGC | AAC | ATC | TGG | CGG | TTT | CCT | TAC | ATA | TGC | TAC | CAG | AAT | GGC | GGA |
|---|---|---|---|---|---|---|---|---|---|---|---|---|---|---|---|
| Leu | Gly | Asn | Ile | Trp | Arg | Phe | Pro | Tyr | Ile | Cys | Tyr | Gln | Asn | Gly | Gly |
|  | 100 |  |  |  |  | 105 |  |  |  |  | 110 |  |  |  |  |

573

| GGG | GCC | TTC | CTC | CTC | CCT | TAT | ACC | ATC | ATG | GCC | ATT | TTC | GGG | GGG | ATC |
|---|---|---|---|---|---|---|---|---|---|---|---|---|---|---|---|
| Gly | Ala | Phe | Leu | Leu | Pro | Tyr | Thr | Ile | Met | Ala | Ile | Phe | Gly | Gly | Ile |
| 115 |  |  |  |  | 120 |  |  |  |  | 125 |  |  |  |  | 130 |

621

| CCG | CTC | TTT | TAC | ATG | GAG | CTC | GCA | CTG | GGC | CAG | TAC | CAC | CGA | AAC | GGG |
|---|---|---|---|---|---|---|---|---|---|---|---|---|---|---|---|
| Pro | Leu | Phe | Tyr | Met | Glu | Leu | Ala | Leu | Gly | Gln | Tyr | His | Arg | Asn | Gly |
|  |  |  |  | 135 |  |  |  |  | 140 |  |  |  |  | 145 |  |

669

| TGC | ATT | TCC | ATA | TGG | AGG | AAG | ATC | TGC | CCG | ATT | TTC | AAA | GGC | ATT | GGT |
|---|---|---|---|---|---|---|---|---|---|---|---|---|---|---|---|
| Cys | Ile | Ser | Ile | Trp | Arg | Lys | Ile | Cys | Pro | Ile | Phe | Lys | Gly | Ile | Gly |
|  |  |  | 150 |  |  |  |  | 155 |  |  |  |  | 160 |  |  |

717

| TAC | GCC | ATC | TGC | ATC | ATC | GCC | TTT | TAC | ATC | GCC | TCC | TAC | TAC | AAC | ACC |
|---|---|---|---|---|---|---|---|---|---|---|---|---|---|---|---|
| Tyr | Ala | Ile | Cys | Ile | Ile | Ala | Phe | Tyr | Ile | Ala | Ser | Tyr | Tyr | Asn | Thr |
|  |  | 165 |  |  |  |  | 170 |  |  |  |  | 175 |  |  |  |

765

| ATC | ATA | GCC | TGG | GCG | CTC | TAC | TAC | CTC | ATC | TCC | TCC | CTC | ACG | GAC | CGG |
|---|---|---|---|---|---|---|---|---|---|---|---|---|---|---|---|
| Ile | Ile | Ala | Trp | Ala | Leu | Tyr | Tyr | Leu | Ile | Ser | Ser | Leu | Thr | Asp | Arg |
|  | 180 |  |  |  |  | 185 |  |  |  |  | 190 |  |  |  |  |

813

| CTG | CCC | TGG | ACC | AGC | TGC | ACG | AAC | TCC | TGG | AAC | ACT | GGC | AAC | TGC | ACC |
|---|---|---|---|---|---|---|---|---|---|---|---|---|---|---|---|
| Leu | Pro | Trp | Thr | Ser | Cys | Thr | Asn | Ser | Trp | Asn | Thr | Gly | Asn | Cys | Thr |
| 195 |  |  |  |  | 200 |  |  |  |  | 205 |  |  |  |  | 210 |

861

| AAC | TAC | TTC | GCC | CAG | GAC | AAC | ATC | ACC | TGG | ACG | CTG | CAT | TCC | ACG | TCC |
|---|---|---|---|---|---|---|---|---|---|---|---|---|---|---|---|
| Asn | Tyr | Phe | Ala | Gln | Asp | Asn | Ile | Thr | Trp | Thr | Leu | His | Ser | Thr | Ser |
|  |  |  |  | 215 |  |  |  |  | 220 |  |  |  |  | 225 |  |

909

| CCC | GCT | GAG | GAG | TTC | TAC | TTG | CGC | CAT | GTC | CTG | CAG | ATC | CAC | CAG | TCT |
|---|---|---|---|---|---|---|---|---|---|---|---|---|---|---|---|
| Pro | Ala | Glu | Glu | Phe | Tyr | Leu | Arg | His | Val | Leu | Gln | Ile | His | Gln | Ser |
|  |  |  | 230 |  |  |  |  | 235 |  |  |  |  | 240 |  |  |

957

| AAG | GGA | CTC | CAG | GAC | CTG | GGC | ACC | ATC | AGC | TGG | CAG | CTG | ACT | CTC | TGC |
|---|---|---|---|---|---|---|---|---|---|---|---|---|---|---|---|
| Lys | Gly | Leu | Gln | Asp | Leu | Gly | Thr | Ile | Ser | Trp | Gln | Leu | Thr | Leu | Cys |
|  |  | 245 |  |  |  |  | 250 |  |  |  |  | 255 |  |  |  |

1005

| ATC | GTG | CTC | ATC | TTC | ACC | GTA | ATC | TAC | TTT | AGC | ATC | TGG | AAA | GGC | GTC |
|---|---|---|---|---|---|---|---|---|---|---|---|---|---|---|---|
| Ile | Val | Leu | Ile | Phe | Thr | Val | Ile | Tyr | Phe | Ser | Ile | Trp | Lys | Gly | Val |
| 260 |  |  |  |  | 265 |  |  |  |  | 270 |  |  |  |  |  |

1053

| AAA | ACA | TCT | GGC | AAG | GTG | GTG | TGG | GTG | ACA | GCC | ACC | TTC | CCA | TAC | ATT |
|---|---|---|---|---|---|---|---|---|---|---|---|---|---|---|---|
| Lys | Thr | Ser | Gly | Lys | Val | Val | Trp | Val | Thr | Ala | Thr | Phe | Pro | Tyr | Ile |
| 275 |  |  |  | 280 |  |  |  |  | 285 |  |  |  |  | 290 |  |

1101

| GTC | CTC | TCT | GTC | CTG | CTG | GTG | AGG | GGG | GCC | ACC | CTT | CCT | GGA | GCC | TGG |
|---|---|---|---|---|---|---|---|---|---|---|---|---|---|---|---|
| Val | Leu | Ser | Val | Leu | Leu | Val | Arg | Gly | Ala | Thr | Leu | Pro | Gly | Ala | Trp |
|  |  |  |  | 295 |  |  |  |  | 300 |  |  |  |  | 305 |  |

1149

| AGA | GGG | GTC | GTC | TTC | TAC | TTG | AAA | CCC | AAC | TGG | CAG | AAA | CTC | TTG | GAG |
|---|---|---|---|---|---|---|---|---|---|---|---|---|---|---|---|
| Arg | Gly | Val | Val | Phe | Tyr | Leu | Lys | Pro | Asn | Trp | Gln | Lys | Leu | Leu | Glu |
|  |  |  | 310 |  |  |  |  | 315 |  |  |  |  | 320 |  |  |

1197

| ACA | GGG | GTG | TGG | GTA | GAT | GCC | GCC | GCT | CAG | ATC | TTC | TTC | TCT | CTT | GGC |
|---|---|---|---|---|---|---|---|---|---|---|---|---|---|---|---|
| Thr | Gly | Val | Trp | Val | Asp | Ala | Ala | Ala | Gln | Ile | Phe | Phe | Ser | Leu | Gly |
|  |  | 325 |  |  |  |  | 330 |  |  |  |  | 335 |  |  |  |

1245

| CCG | GGC | TTT | GGG | GTT | CTC | CTG | GCT | TTT | GCT | AGC | TAC | AAC | AAG | TTC | AAC |
|---|---|---|---|---|---|---|---|---|---|---|---|---|---|---|---|
| Pro | Gly | Phe | Gly | Val | Leu | Leu | Ala | Phe | Ala | Ser | Tyr | Asn | Lys | Phe | Asn |
|  | 340 |  |  |  |  | 345 |  |  |  |  | 350 |  |  |  |  |

1293

| AAC | AAC | TGT | TAC | CAA | GAT | GCC | CTG | GTG | ACC | AGT | GTG | GTG | AAC | TGC | ATG |
|---|---|---|---|---|---|---|---|---|---|---|---|---|---|---|---|
| Asn | Asn | Cys | Tyr | Gln | Asp | Ala | Leu | Val | Thr | Ser | Val | Val | Asn | Cys | Met |
| 355 |  |  |  |  | 360 |  |  |  |  | 365 |  |  |  |  | 370 |

1341

| ACA | AGC | TTC | GTC | TCT | GGC | TTC | GTC | ATC | TTC | ACG | GTG | CTT | GGC | TAC | ATG |
|---|---|---|---|---|---|---|---|---|---|---|---|---|---|---|---|
| Thr | Ser | Phe | Val | Ser | Gly | Phe | Val | Ile | Phe | Thr | Val | Leu | Gly | Tyr | Met |

1389

|  |  |  |  |  |  | 375 |  |  |  |  |  | 380 |  |  |  |  |  | 385 |  |  |  |
|---|---|---|---|---|---|---|---|---|---|---|---|---|---|---|---|---|---|---|---|---|---|---|
| GCG | GAG | ATG | AGG | AAT | GAA | GAT | GTG | TCA | GAG | GTG | GCC | AAA | GAC | GCA | GGC |  |  |  |  |  | 1437 |
| Ala | Glu | Met | Arg | Asn | Glu | Asp | Val | Ser | Glu | Val | Ala | Lys | Asp | Ala | Gly |  |  |  |  |  |  |
|  |  |  | 390 |  |  |  |  | 395 |  |  |  |  | 400 |  |  |  |  |  |  |  |  |
| CCC | AGC | CTC | CTC | TTC | ATC | ACG | TAT | GCA | GAG | GCA | ATA | GGC | AAC | ATG | CCA |  |  |  |  |  | 1485 |
| Pro | Ser | Leu | Leu | Phe | Ile | Thr | Tyr | Ala | Glu | Ala | Ile | Gly | Asn | Met | Pro |  |  |  |  |  |  |
|  |  | 405 |  |  |  |  | 410 |  |  |  |  | 415 |  |  |  |  |  |  |  |  |  |
| GCA | TCC | ACG | TTC | TTT | GCC | ATC | ATC | TTC | TTC | CTC | ATG | TTA | ATC | ACG | CTG |  |  |  |  |  | 1533 |
| Ala | Ser | Thr | Phe | Phe | Ala | Ile | Ile | Phe | Phe | Leu | Met | Leu | Ile | Thr | Leu |  |  |  |  |  |  |
|  |  | 420 |  |  |  | 425 |  |  |  |  | 430 |  |  |  |  |  |  |  |  |  |  |
| GGA | TTG | GAC | AGC | ACG | TTC | GCA | GGC | CTG | GAA | GGT | GTG | ATC | ACA | GCT | GTG |  |  |  |  |  | 1581 |
| Gly | Leu | Asp | Ser | Thr | Phe | Ala | Gly | Leu | Glu | Gly | Val | Ile | Thr | Ala | Val |  |  |  |  |  |  |
| 435 |  |  |  | 440 |  |  |  |  | 445 |  |  |  |  | 450 |  |  |  |  |  |  |  |
| CTG | GAT | GAG | TTC | CCT | CAC | ATC | TGG | GCC | AAG | CGC | AGG | GAA | TGG | TTC | GTG |  |  |  |  |  | 1629 |
| Leu | Asp | Glu | Phe | Pro | His | Ile | Trp | Ala | Lys | Arg | Arg | Glu | Trp | Phe | Val |  |  |  |  |  |  |
|  |  |  |  | 455 |  |  |  |  | 460 |  |  |  |  | 465 |  |  |  |  |  |  |  |
| CTC | ATC | GTG | GTC | ATC | ACG | TGC | GTC | TTG | GGA | TCC | CTC | TCA | CTG | ACG |  |  |  |  |  |  | 1677 |
| Leu | Ile | Val | Val | Ile | Thr | Cys | Val | Leu | Gly | Ser | Leu | Leu | Thr | Leu | Thr |  |  |  |  |  |  |
|  |  |  | 470 |  |  |  |  | 475 |  |  |  |  | 480 |  |  |  |  |  |  |  |  |
| TCA | GGA | GGG | GCA | TAC | GTG | GTG | ACT | CTG | CTG | GAG | GAG | TAT | GCC | ACG | GGG |  |  |  |  |  | 1725 |
| Ser | Gly | Gly | Ala | Tyr | Val | Val | Thr | Leu | Leu | Glu | Glu | Tyr | Ala | Thr | Gly |  |  |  |  |  |  |
|  |  | 485 |  |  |  |  | 490 |  |  |  |  | 495 |  |  |  |  |  |  |  |  |  |
| CCA | GCA | GTG | CTC | ACC | GTG | GCC | CTC | ATC | GAG | GCC | GTC | GCC | GTG | TCT | TGG |  |  |  |  |  | 1773 |
| Pro | Ala | Val | Leu | Thr | Val | Ala | Leu | Ile | Glu | Ala | Val | Ala | Val | Ser | Trp |  |  |  |  |  |  |
|  |  | 500 |  |  |  |  | 505 |  |  |  |  | 510 |  |  |  |  |  |  |  |  |  |
| TTC | TAT | GGA | ATC | ACT | CAG | TTC | TGC | AGC | GAT | GTG | AAG | GAG | ATG | CTG | GGC |  |  |  |  |  | 1821 |
| Phe | Tyr | Gly | Ile | Thr | Gln | Phe | Cys | Ser | Asp | Val | Lys | Glu | Met | Leu | Gly |  |  |  |  |  |  |
| 515 |  |  |  |  | 520 |  |  |  |  | 525 |  |  |  |  | 530 |  |  |  |  |  |  |
| TTC | AGC | GGG | ATG | GTT | TGG | AGG | ATC | TGC | TGG | GTG | GCC | ATC | AGC | CCT | CTG |  |  |  |  |  | 1869 |
| Phe | Ser | Gly | Met | Val | Trp | Arg | Ile | Cys | Trp | Val | Ala | Ile | Ser | Pro | Leu |  |  |  |  |  |  |
|  |  |  |  | 535 |  |  |  |  | 540 |  |  |  |  | 545 |  |  |  |  |  |  |  |
| TTT | CTC | CTG | TTC | ATC | ATT | TGC | AGT | TTT | CTG | ATG | AGC | CCA | CCC | CAG | CTA |  |  |  |  |  | 1917 |
| Phe | Leu | Leu | Phe | Ile | Ile | Cys | Ser | Phe | Leu | Met | Ser | Pro | Pro | Gln | Leu |  |  |  |  |  |  |
|  |  |  | 550 |  |  |  |  | 555 |  |  |  |  | 560 |  |  |  |  |  |  |  |  |
| CGG | CTT | TTC | CAA | TAC | AAC | TAT | CCC | CAC | TGG | AGT | ATC | GTC | TTG | GGC | TAC |  |  |  |  |  | 1965 |
| Arg | Leu | Phe | Gln | Tyr | Asn | Tyr | Pro | His | Trp | Ser | Ile | Val | Leu | Gly | Tyr |  |  |  |  |  |  |
|  |  | 565 |  |  |  |  | 570 |  |  |  |  | 575 |  |  |  |  |  |  |  |  |  |
| TGC | ATA | GGG | ATG | TCG | TCC | GTC | ATC | TGC | ATC | CCT | ACC | TAT | ATC | ATT | TAT |  |  |  |  |  | 2013 |
| Cys | Ile | Gly | Met | Ser | Ser | Val | Ile | Cys | Ile | Pro | Thr | Tyr | Ile | Ile | Tyr |  |  |  |  |  |  |
| 580 |  |  |  |  | 585 |  |  |  |  | 590 |  |  |  |  |  |  |  |  |  |  |  |
| CGG | CTG | ATC | AGC | ACT | CCG | GGG | ACA | CTT | AAG | GAG | CGG | ATT | ATT | AAA | AGT |  |  |  |  |  | 2061 |
| Arg | Leu | Ile | Ser | Thr | Pro | Gly | Thr | Leu | Lys | Glu | Arg | Ile | Ile | Lys | Ser |  |  |  |  |  |  |
| 595 |  |  |  |  | 600 |  |  |  |  | 605 |  |  |  |  | 610 |  |  |  |  |  |  |
| ATC | ACT | CCT | GAA | ACA | CCC | ACA | GAA | ATC | CGT | GTG | GGA | CAT | CCG | CAT | GAA |  |  |  |  |  | 2109 |
| Ile | Thr | Pro | Glu | Thr | Pro | Thr | Glu | Ile | Arg | Val | Gly | His | Pro | His | Glu |  |  |  |  |  |  |
|  |  |  |  | 615 |  |  |  |  | 620 |  |  |  |  | 625 |  |  |  |  |  |  |  |
| TGC | TGT | GTA | ACA | CAC | CCT | GGG | AGA | GGA | CAC | CTC | TTC | CCA | GCC | ACC | TCT |  |  |  |  |  | 2157 |
| Cys | Cys | Val | Thr | His | Pro | Gly | Arg | Gly | His | Leu | Phe | Pro | Ala | Thr | Ser |  |  |  |  |  |  |
|  |  |  | 630 |  |  |  |  | 635 |  |  |  |  | 640 |  |  |  |  |  |  |  |  |
| CTC | AGC | TCT | GAA | AAG | CCC | ACT | GGA | CTC | CTC | CTC | TAAGCAAGCT | GATGAAGACA |  |  |  |  |  |  |  |  | 2210 |
| Leu | Ser | Ser | Glu | Lys | Pro | Thr | Gly | Leu | Leu | Leu |  |  |  |  |  |  |  |  |  |  |  |
|  |  | 645 |  |  |  |  | 650 |  |  |  |  |  |  |  |  |  |  |  |  |  |  |
| CGTCTAACAC | TATGTGCCAG | ACTCTGTGGA | TCCGACCACT | TCTTTCCGTG | GACTCTCAGA |  |  |  |  |  |  |  |  |  |  |  |  |  |  |  | 2270 |
| CATGCTACCA | CATTCGATGG | TGACACCACT | GAGCTGGCCT | CTTGGACACG | TCAGGGAGTG |  |  |  |  |  |  |  |  |  |  |  |  |  |  |  | 2330 |
| GAAGGAGGGA | TGAACGCCAC | CCAGTCATTC | AGCTAGCTTC | AGTTTAGAAT | TAGGTCTGTG |  |  |  |  |  |  |  |  |  |  |  |  |  |  |  | 2390 |
| AGAGTCTGTT | ACTAGTTTTT | GGTAAGTACT | AACTACCCCG | CATCTGTTAG | CTTCTAAAGC |  |  |  |  |  |  |  |  |  |  |  |  |  |  |  | 2450 |
| CTTCAATGTT | CATGAATACA | TAAACCACCT | AAGAGAAAAC | ATATATGTCT | TGCTAGCCAT |  |  |  |  |  |  |  |  |  |  |  |  |  |  |  | 2510 |

-continued

```
ATATATTTTC  TCGGTAGCAT  AGAATTCTAT  AGCTGGAATC  TCCTAGAACC  CTGTAACCCA      2570

CGTGCTGCTG  TGAGGTTAAG  GAGGGAAGGT  GTAAGGATTG  CTACACTGAA  AAAATGGTGT      2630

ATATGTGTGA  GCTATTGTGT  CTGTCCATTA  TCGTCTGTGA  GCCCTCGATC  CCAATACTCC      2690

AGGTCCATTT  CAAACTGTAT  AAATGGCCTC  TAATTTTTCT  TACATTAAAC  AGATTCTACC      2750

TAAAAA                                                                    2756
```

( 2 ) INFORMATION FOR SEQ ID NO:2:

( i ) SEQUENCE CHARACTERISTICS:
        ( A ) LENGTH: 653 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Glu  Thr  Thr  Pro  Leu  Asn  Ser  Gln  Lys  Val  Leu  Ser  Glu  Cys  Lys
 1                   5                  10                  15

Asp  Arg  Glu  Asp  Cys  Gln  Glu  Asn  Gly  Val  Leu  Gln  Lys  Gly  Val  Pro
                20                  25                  30

Thr  Thr  Ala  Asp  Arg  Ala  Glu  Pro  Ser  Gln  Ile  Ser  Asn  Gly  Tyr  Ser
           35                  40                  45

Ala  Val  Pro  Ser  Thr  Ser  Ala  Gly  Asp  Glu  Ala  Ser  His  Ser  Ile  Pro
     50                  55                  60

Ala  Ala  Thr  Thr  Thr  Leu  Val  Ala  Glu  Ile  Arg  Gln  Gly  Glu  Arg  Glu
65                   70                  75                        80

Thr  Trp  Gly  Lys  Lys  Met  Asp  Phe  Leu  Leu  Ser  Val  Ile  Gly  Tyr  Ala
                85                  90                  95

Val  Asp  Leu  Gly  Asn  Ile  Trp  Arg  Phe  Pro  Tyr  Ile  Cys  Tyr  Gln  Asn
               100                 105                 110

Gly  Gly  Gly  Ala  Phe  Leu  Leu  Pro  Tyr  Thr  Ile  Met  Ala  Ile  Phe  Gly
          115                 120                 125

Gly  Ile  Pro  Leu  Phe  Tyr  Met  Glu  Leu  Ala  Leu  Gly  Gln  Tyr  His  Arg
     130                 135                 140

Asn  Gly  Cys  Ile  Ser  Ile  Trp  Arg  Lys  Ile  Cys  Pro  Ile  Phe  Lys  Gly
145                 150                 155                      160

Ile  Gly  Tyr  Ala  Ile  Cys  Ile  Ile  Ala  Phe  Tyr  Ile  Ala  Ser  Tyr  Tyr
               165                 170                 175

Asn  Thr  Ile  Ile  Ala  Trp  Ala  Leu  Tyr  Tyr  Leu  Ile  Ser  Ser  Leu  Thr
          180                 185                 190

Asp  Arg  Leu  Pro  Trp  Thr  Ser  Cys  Thr  Asn  Ser  Trp  Asn  Thr  Gly  Asn
     195                 200                 205

Cys  Thr  Asn  Tyr  Phe  Ala  Gln  Asp  Asn  Ile  Thr  Trp  Thr  Leu  His  Ser
210                 215                 220

Thr  Ser  Pro  Ala  Glu  Glu  Phe  Tyr  Leu  Arg  His  Val  Leu  Gln  Ile  His
225                 230                 235                      240

Gln  Ser  Lys  Gly  Leu  Gln  Asp  Leu  Gly  Thr  Ile  Ser  Trp  Gln  Leu  Thr
               245                 250                 255

Leu  Cys  Ile  Val  Leu  Ile  Phe  Thr  Val  Ile  Tyr  Phe  Ser  Ile  Trp  Lys
          260                 265                 270

Gly  Val  Lys  Thr  Ser  Gly  Lys  Val  Val  Trp  Val  Thr  Ala  Thr  Phe  Pro
     275                 280                 285

Tyr  Ile  Val  Leu  Ser  Val  Leu  Leu  Val  Arg  Gly  Ala  Thr  Leu  Pro  Gly
     290                 295                 300

Ala  Trp  Arg  Gly  Val  Val  Phe  Tyr  Leu  Lys  Pro  Asn  Trp  Gln  Lys  Leu
```

-continued

| 305 | | | | 310 | | | | | 315 | | | | 320 |
|---|---|---|---|---|---|---|---|---|---|---|---|---|---|
| Leu | Glu | Thr | Gly | Val | Trp | Val | Asp | Ala | Ala | Gln | Ile | Phe | Phe | Ser |
| | | | | 325 | | | | 330 | | | | 335 | |
| Leu | Gly | Pro | Gly | Phe | Gly | Val | Leu | Leu | Ala | Phe | Ala | Ser | Tyr | Asn | Lys |
| | | | 340 | | | | 345 | | | | | 350 | |
| Phe | Asn | Asn | Asn | Cys | Tyr | Gln | Asp | Ala | Leu | Val | Thr | Ser | Val | Val | Asn |
| | | 355 | | | | 360 | | | | | 365 | | |
| Cys | Met | Thr | Ser | Phe | Val | Ser | Gly | Phe | Val | Ile | Phe | Thr | Val | Leu | Gly |
| | 370 | | | | 375 | | | | | 380 | | | |
| Tyr | Met | Ala | Glu | Met | Arg | Asn | Glu | Asp | Val | Ser | Glu | Val | Ala | Lys | Asp |
| 385 | | | | 390 | | | | | 395 | | | | 400 |
| Ala | Gly | Pro | Ser | Leu | Leu | Phe | Ile | Thr | Tyr | Ala | Glu | Ala | Ile | Gly | Asn |
| | | | 405 | | | | 410 | | | | | 415 | |
| Met | Pro | Ala | Ser | Thr | Phe | Phe | Ala | Ile | Ile | Phe | Phe | Leu | Met | Leu | Ile |
| | | | 420 | | | | 425 | | | | | 430 | |
| Thr | Leu | Gly | Leu | Asp | Ser | Thr | Phe | Ala | Gly | Leu | Glu | Gly | Val | Ile | Thr |
| | | 435 | | | | 440 | | | | | 445 | | |
| Ala | Val | Leu | Asp | Glu | Phe | Pro | His | Ile | Trp | Ala | Lys | Arg | Arg | Glu | Trp |
| | 450 | | | | 455 | | | | | 460 | | | |
| Phe | Val | Leu | Ile | Val | Val | Ile | Thr | Cys | Val | Leu | Gly | Ser | Leu | Leu | Thr |
| 465 | | | | 470 | | | | | 475 | | | | 480 |
| Leu | Thr | Ser | Gly | Gly | Ala | Tyr | Val | Val | Thr | Leu | Leu | Glu | Glu | Tyr | Ala |
| | | | 485 | | | | 490 | | | | | 495 | |
| Thr | Gly | Pro | Ala | Val | Leu | Thr | Val | Ala | Leu | Ile | Glu | Ala | Val | Ala | Val |
| | | | 500 | | | | 505 | | | | | 510 | |
| Ser | Trp | Phe | Tyr | Gly | Ile | Thr | Gln | Phe | Cys | Ser | Asp | Val | Lys | Glu | Met |
| | | 515 | | | | 520 | | | | | 525 | | |
| Leu | Gly | Phe | Ser | Gly | Met | Val | Trp | Arg | Ile | Cys | Trp | Val | Ala | Ile | Ser |
| | 530 | | | | 535 | | | | | 540 | | | |
| Pro | Leu | Phe | Leu | Leu | Phe | Ile | Ile | Cys | Ser | Phe | Leu | Met | Ser | Pro | Pro |
| 545 | | | | | 550 | | | | | 555 | | | | 560 |
| Gln | Leu | Arg | Leu | Phe | Gln | Tyr | Asn | Tyr | Pro | His | Trp | Ser | Ile | Val | Leu |
| | | | 565 | | | | | 570 | | | | | 575 |
| Gly | Tyr | Cys | Ile | Gly | Met | Ser | Ser | Val | Ile | Cys | Ile | Pro | Thr | Tyr | Ile |
| | | 580 | | | | | 585 | | | | | 590 | |
| Ile | Tyr | Arg | Leu | Ile | Ser | Thr | Pro | Gly | Thr | Leu | Lys | Glu | Arg | Ile | Ile |
| | | 595 | | | | 600 | | | | | 605 | | |
| Lys | Ser | Ile | Thr | Pro | Glu | Thr | Pro | Thr | Glu | Ile | Arg | Val | Gly | His | Pro |
| | 610 | | | | 615 | | | | | 620 | | | |
| His | Glu | Cys | Cys | Val | Thr | His | Pro | Gly | Arg | Gly | His | Leu | Phe | Pro | Ala |
| 625 | | | | 630 | | | | | 635 | | | | 640 |
| Thr | Ser | Leu | Ser | Ser | Glu | Lys | Pro | Thr | Gly | Leu | Leu | Leu |
| | | | 645 | | | | 650 | | |

( 2 ) INFORMATION FOR SEQ ID NO:3:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO

```
( i x ) FEATURE:
        ( A ) NAME/KEY: -
        ( B ) LOCATION: 1..62
        ( D ) OTHER INFORMATION: /label=screening_oligo
                / note="synthetic degenerate oligonucleotide used
                to screen candidate clones for serotonin
                transporter cDNA."

( x i ) SEQUENCE DESCRIPTION: SEQ ID NO:3:

TAGGGGATCA  GGAAGGCGCC  GCCNCCRTTY  TTNYMRCACA  GGTAGGGGAA  CCGCCACACA           60

TT                                                                              62

( 2 ) INFORMATION FOR SEQ ID NO:4:

( i ) SEQUENCE CHARACTERISTICS:
                ( A ) LENGTH: 51 base pairs
                ( B ) TYPE: nucleic acid
                ( C ) STRANDEDNESS: single
                ( D ) TOPOLOGY: linear ( i i ) MOLECULE TYPE: DNA (synthetic)

( i i i ) HYPOTHETICAL: NO ( i v ) ANTI-SENSE: YES ( i x ) FEATURE:
                ( A ) NAME/KEY: -
                ( B ) LOCATION: 1..51
                ( D ) OTHER INFORMATION: /label=ishh_oligo
                        / note="synthetic oligonucleotide used for in situ
                        hybridization studies of serotonin transporter
                        mRNA expression."

( x i ) SEQUENCE DESCRIPTION: SEQ ID NO:4:

CCTGCACTTG  TGCTGGGGAC  TGCAGAGTAC  CCATTGGATA  TTTGGCTAGG  C                   51

( 2 ) INFORMATION FOR SEQ ID NO:5:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( i i ) MOLECULE TYPE: DNA (synthetic)

( i v ) ANTI-SENSE: NO ( i x ) FEATURE:
                ( A ) NAME/KEY: -
                ( B ) LOCATION: 1..51
                ( D ) OTHER INFORMATION: /label=oligonucleotide
                        / note="synthetic oligonucleotide putatively useful for
                        the mutagenesis of leu132 of rat serotonin transporter
                        protein to an alanine."

( x i ) SEQUENCE DESCRIPTION: SEQ ID NO:5:

CCTTATACCA  TCATGGCCAT  TTTCGGGGGG  ATCCGCGCT  TTTACATGGA  GCTC                 54
```

CDNA CLONE OF A RAT SEROTONIN TRANSPORTER AND PROTEIN ENCODED THEREBY

FIELD OF THE INVENTION

The present invention relates to a polypeptide which confers upon cells the ability to import serotonin and related compounds from the extracellular environment into the cells. The invention also relates to a cDNA clone which encodes the serotonin transporter protein.

BACKGROUND OF THE INVENTION:

Scientific publications described in this application are incorporated in full by reference thereto.

Following their release and action on receptors, monoamine neurotransmitters are taken up from the synaptic cleft into pre-synaptic terminals by plasma membrane transporters. This re-uptake terminates the action of the neurotransmitter. Uptake mechanisms for radiolabeled biogenic amines were first demonstrated by Axelrod and co-workers for noradrenaline Axelrod, J. and Hertting, G., *Nature*, 192, 172 (1961); Axelrod, J., *Science* 173, 589 (1971)), and subsequently, for serotonin by several groups (Axelrod, J. and Inscoe, J. K., *J. Pharmacol. Exp. Ther.* 141, 161 (1963); Aghajanian G. K. and Bloom, F. E., *J. Pharmacol. Exp. Ther.* 156, 23 (1967); Blackburn, K. J. et al., *Life Sci.* 6, 1653 (1967)).

In addition to its role in removing serotonin (5-HT) from the synaptic cleft, the 5-HT transporter (5HTT) allows platelets and rodent mast cells to concentrate 5-HT (Pletscher, A., *Int. J. Cardiol.* 14, 177 (1987)). These cells store and secrete large amounts of the amine, but do not synthesize it.

5-HT transporters are a site of action for some antidepressants and drugs of abuse such as amphetamines and cocaine.

A cDNA library was constructed from rat basophilic leukemia cell (RBL 2H3, a cognate mast cell) mRNA in pCDM7 (Kanner, B. I. and Bendahan, A., *Biochim. Biophys. Acta*, 816, 403 (1985) and pools of recombinants were screened by expression of recombinant plasmid-encoded proteins in COS cells. The pCDM7 vector is the same as pCDM8 (Seed, B., *Nature* 329, 840 (1987)) but without the polyoma origin and a BamHI site. In this vector, cDNAs can be expressed from either the T7 RNA polymerase or the cytomegalovirus virus (CM) promoter. Expression from the T7 polymerase promoter can be accomplished either by transfection into cells expressing T7 polymerase or by in vitro transcription from the T7 promoter ("Protocols and Applications Guide", c. 1991 by Promega Corporation) and microinjection of the synthetic mRNA into a recipient cell.

Poly(A) enriched RNA was prepared from RBL 2H3 cells (cognate mast cell) using guanidinium isothiocyanate followed by oligo(dT) cellulose chromatography (Okayama, H. et al, *Methods in Enzymology* (Academic Press, Inc., New York) 154, 3 (1987)). Double-stranded cDNA was synthesized from 5 ug RBL 2H3 poly(A)+RNA using Murine moloney reverse transcriptase (Superscript, BRL) and Avian myoblastosis virus reverse transcriptase H.C. (Promega) by the method of U. Gubler and B. J. Hoffman (*Gene* 25, 263 (1983)). BstXI adaptors (Invitrogen) were ligated to blunt-ended cDNA and size-fractionated on a potassium acetate gradient. cDNA (>1.5 kb) was ligated into BstXI-digested pCDM7 and electroporated into *Escherichia coli* MC1061p3 to yield a library of $2.3 \times 10^6$ recombinants.

Plasmid DNA from twenty-four pools of 13,000 recombinants was prepared by Triton X-100 lysis and cesium chloride banding (Chen, C. and Okayama, H., *Mol. Cell Biol.* 7, 2745 (1982)). DNA (3.3 ug) from each subdivision was transfected onto $2 \times 10^5$ COS-7 cells in single chamber slides (Lab-Tek) by calcium phosphate precipitation (ibid). After 72 h, cells were washed with uptake buffer consisting of 25 mM Hepes, pH 7.4, 125 mM NaCl, 4.8 mM KCl, 1.2 mM $KH_2PO_4$, 1.3 mM $CaCl_2$, 1.2 mM $MgSO_4$, 5.6 mM glucose, 1 mM Na ascorbate and 10 uM pargyline, then pre-incubated in uptake buffer for 15 min. Cells were incubated for 2 h with $^3$H-5-HT (100 nM) at 37° C. followed by three 1 ml washes on ice, fixed in 2.5% glutaraldehyde in PBS with acrolein (1:100) for 30 min at 23° C. and washed in phosphate-buffered saline (PBS). Following an $H_2O$ dip to remove salts, slides were air-dried, coated with nuclear emulsion (NTB2, Kodak) and exposed for 2 days. A single positive pool was identified microscopically and further subdivided. At the level of 100 clones per pool, subdivisions were screened using the recombinant T7 RNA polymerase-containing vaccinia virus (Fuerst, T. R. et al., *Proc. Natl. Acad. Sci. USA* 83, 8122 (1986); Fuerst, T. R. et al., *Mol. Cell Biol.* 7, 2538 (1987)). $2 \times 10^5$ CV-1 cells were plated in 6 well plates, infected with T7 RNA polymerase-containing vaccinia virus at a multiplicity of infection of 10 pfu per cell. After 30 min, cells were transfected with 3 ug plasmid DNA isolated from pooled clones of the pCDM7 cDNA transformants using 10 ug lipofectin (BRL). After 24–30 h., cells were assayed for serotonin uptake as described above. Following washes, cells were solubilized in 0.5N NaOH and radioactivity determined by liquid scintillation counting.

In parallel with the functional assay of cDNA clones, subdivisions were screened with a degenerate oligonucleotide:

5'-taggggatca ggaaggcgcc gccnccrtty ttnymrcaca ggtagggga ccgc-cacaca tt-3'

(SEQ. ID. NO. 3) directed at a region highly conserved in noradrenaline (Pacholczyk, T. et al., *Nature* 350, 350 (1991)) and GABA transporters (Guastella, J. et al., *Science* 249, 1303 (1990), Nelson, H. et al., *FEBS Lett.* 269, 181 (1990)). A single hybridizing band was present in each positive pool identified by bioassay through three successive rounds of screening. Screening with the kinased consensus oligonucleotide probe was performed in 6× SSC and 2× Denhardt's solution at 60° C. A single positive clone was identified from a positive pool of 100 clones using this consensus oligonucleotide.

B. Sequence Analysis at 5HTT encoding cDNA

5HTT cDNA was subcloned into M13 bacteriophage and sequenced completely on both strands using the Sequenase kit (US Biochemicals). Sequence analysis was performed with the University of Wisconsin Genetics Computer Group Sequence Analysis Package, version 7.0 (1991).

Sequence analysis of the 3.0 kilobase (kb) insert revealed an open reading frame of 1,959 base pairs (bp) (FIG. 2) (SEQ. ID. NO. 1), predicting a protein of 653 amino acids with a relative molecular mass of ~73,000 (73 kD) excluding glycosylation. The initiating ATG is 52 bases downstream from a stop codon, and the surrounding sequence conforms to a consensus translation initiation site (Kozak, M., *Nucleic Acids Res.* 15, 8125 (1987)). Hydropathy analysis (Kyte, J. and Doolittle, R. F., *J. Mol. Biol.* 157, 105 (1982)) indicates 12–13 potential transmembrane domains with no apparent signal sequence (von Heijne, G., Eur. J. Biochem. 133, 17 (1983)). On this basis and by analogy to GABA and noradrenaline transporters (GAT-1 and NET, respectively), the amino- and carboxy-termini, which have potential protein kinase C phosphorylation sites, may be located intracellularly; a large loop with two potential glycosylation sites would then be found extracellularly.

EXAMPLE 2

Determining the pattern of 5HTT expression in vivo

Serotonergic cell bodies are found in the midline raphe nuclei of the brainstem. These cells innervate virtually all areas of the central nervous system (Steinbusch, H. W. M., in *Handbook of Chemical Neuroanatomy*, A. Bjorklund et al., Eds. (Elsevier, New York, 1984), vol. 3, pp. 68–125.). In situ hybridization histochemistry (ISHH) on sagittal brain sections (FIG. 3) and peripheral organs (not shown) using a 5HTT-specific oligonucleotide was performed using the 51 base oligonucleotide 5'-CCTGCACTTGTGCTGGGGACTGCAGAG-TACCCATTGGATATTTGGCTAGGC-3' as probe (SEQ. ID. NO. 4). ISHH indicates that 5-HT transporters are present in peripheral tissues and in brain. In the brain, 5HTT mRNA appears to be found exclusively in areas with serotonergic neurons. Some individual cells have very high levels of mRNA while there is no detectable signal in other neurons. High levels of mRNA are also present in the lamina propria of the stomach and the duodenum, and in chromaffin cells of the adrenal gland.

Northern blot analysis was performed as follows:

Poly(A) enriched RNA (2 ug) from tissues and brain regions was size-fractionated by formaldehyde agarose gel electrophoresis and transferred to Nytran membrane (Schleicher and Schuell) by electroblotting. Northern blots were hybridized to a nick translated 2.2 kb EcoRI fragment from the 5HTT cDNA for 20 h. at 42° C. in 50% formamide, 5× SSPE, 5× Denhardt's solution, 0.1% SDS, 500 ug/ml sheared salmon sperm DNA and 250 ug/ml yeast tRNA, and washed in 0.2× SSC at 60° C. RNA standards (BRL) were run in parallel and stained with ethidium bromide. Blots were exposed for 3 days.

With the oligonucleotide used for ISHH revealed a single hybridizing band of 3.1 kb in both brain and peripheral tissues. In order to detect lower levels of mRNA, the Northern blots were re-probed with a nick-translated EcoRI fragment containing the entire coding region (FIG. 4). In the CNS, high levels of mRNA are expressed in the brainstem where serotonergic cell bodies are localized, but no hybridization was detected in other brain regions. Gut and lung have very high levels of 5HTT mRNA, spleen has an intermediate level while low levels of mRNA are present in stomach, uterus and kidney. $^3$H-5-HT uptake has been reported in lung artery endothelium, in serotonergic neurons and enterochromaffin cells of the gut, and, as noted above, in rodent mast cells and macrophages (Jackson, J. C. et al, *Life Sci.* 42, 1641 (1988); Verbeuren, T. J., in *The Peripheral Actions of 5-Hydroxytryptamine*, J. R. Fozard, Ed. (Oxford University Press, New York, 1989), pp. 1–25.). However, the cell type(s) which have 5HTT mRNA in the gut, lung and spleen remains to be determined.

EXAMPLE 3

Pharmacologic Profile of 5HTT

Uptake studies were performed using CV-1 cells transfected with the 5HTT cDNA. Uptake by the transfected cells had many of the characteristics observed for 5-HT uptake by platelets and brain synaptosomes. $^3$H-5-HT uptake is Na$^+$- and Cl- -dependent (Substitution of Na$^+$ with choline or Li$^+$ decreases uptake by 98% and 85%, respectively. When Cl$^-$ is replaced by acetate, uptake is abolished (99% decrease), while nitrate can partially substitute for chloride (only 52% decrease).

Pharmacological evaluation was performed on 1.4×10$^5$ CV-1 cells plated in 24 well plates as described for library screening. The cells were infected with vaccinia virus containing T7 RNA polymerase and transfected with 5HTT cDNA. Transfected cells were incubated with $^3$H-5-HT (50–100nM) with or without inhibitors for 15 min. Values are the mean±SEM from three determinations performed in triplicate. Non-specific uptake was defined as uptake in the presence of 1 uM paroxetine. K$_i$ values were calculated from IC$_{50}$s according to Cheng and Prusoff (Cheng, Y. and Prusoff, W. H., *Biochem. Pharmacol.* 22, 3099 (1973)). Radioligand incubations were for 15 min (linear range of uptake). Uptake velocity was determined using $^3$H-5-HT concentrations ranging from 0.1 nM to 10 uM (6 logs). K$_m$ and IC$_{50}$'s were determined using Inplot version 3.04 (GraphPAD). Uptake is saturable, exhibiting a K$_m$ of 529+/-107 nM (mean +/- SEM)(20), comparable to that determined in RBL 2H3 (Kanner, B. I. and Bendahan, A., *Biochim. Biophys. Acta* 816, 403 (9185)) and in rat synaptosomes (Hyttel, J., *Neuro-psychopharmacol. Biol. Psychiat.*, 6, 277 (1982); Wodd, M. D. et al, *Neuropharmacology* 25, 519 (1986)).

TABLE 1

Drug affinities for inhibition of 5-HT uptake in CV-1 cells transfected with the 5-HT transporter cDNA.

| Inhibitor | K$_i$ (nM) |
| --- | --- |
| paroxetine | 3.1 ± 0.8 |
| citalopram | 6.1 ± 1.0 |
| clomipramine | 7.1 ± 2.0 |
| fluoxetine | 33 ± 1.0 |
| S(+)fenfluramine | 129 ± 28 |
| ± MDMA | 186 ± 27 |
| imipramine | 209 ± 28 |
| amitriptyline | 262 ± 66 |
| zimelidine | 382 ± 100 |
| mazindol | 548 ± 120 |
| cocaine | 1080 ± 150 |
| desipramine | 1680 ± 400 |
| doxepin | 1850 ± 570 |
| d-amphetamine | 3180 ± 440 |
| reserpine | >10,000 |
| dopamine | >10,000 |
| noradrenaline | >10,000 |

Uptake is potently inhibited by fluoxetine, paroxetine, citalopram and clomipramine, which are highly specific for the 5-HT transporter (Table 1). Fenfluramine, an effective anorectic drug, (Cooper, S. J., *Trends Pharmacol. Sci.* 10, 56 (1989)) also blocks uptake. Antidepressants more selective for noradrenaline and dopamine transporters (Andersen, P. H., *Eur. J. Pharmacol.* 166, 493 (1989)), such as mazindol and desipramine, have lower affinity for the 5-HT transporter. Dopamine and noradrenaline as well as reserpine, an inhibitor of vesicular uptake, are ineffective at blocking 5-HT uptake.

Amphetamine and amphetamine derivatives are substrates for transport by the 5-HT transporter and stimulate release of 5-HT (Steele, T. D. et al., *Biochem. Pharmacol.* 36, 2297 (1987); Nichols, D. E. et al., *J. Med. Chem.* 25, 530 (1982)). 3,4 -Methylenedioxy-methamphetamine (MDMA, "ecstasy") is a potent neurotoxin of serotonergic neurons which causes irreversible cell degeneration, and exhibits potent inhibition of $^3$H-5-HT uptake in cells transfected with the 5HTT cDNA (Table 4). Another drug of abuse, cocaine, is also a relatively potent inhibitor of 5-HT uptake. Although the reinforcing effects of cocaine have been attributed to inhibition of dopamine uptake (Kuhar, M. J. et al., *Trends Neurosci.* 14, 299 (1991)), evidence suggests that blockade of 5-HT transport may play a role in some aspects of cocaine addiction (Cunningham, K. A. and Lakoski, J. M., *Neuropsychopharmacology* 3, 41 (1990); Carroll, M. E. et al., *Pharmacol. Biochem. Behav.* 35, 237 (1990)).

Alternative means of assaying the effect of a compound upon the activity of the serotonin transporter include measurement of inhibition of binding of labelled serotonin to membrane preparations obtained from tissues expressing 5HTT or from cells transfected with 5HTT cDNA. Such membranes can be prepared by the method of Teitler, et al. (Teitler, M. et al., J. Neurochem. (1990)). Membrane preparations may also be used in patch clamp measurements of serotonin transporter activity, as described by Neher and Sakmann (Hamill, O. P. et al, Pfluegers Arch. 391, 85 (1981)). A third assay of serotonin transporter activity is measurement of cytotoxicity due to MDMA or 5,7 DHT import into cells transfected with the 5HTT cDNA. Many cytotoxicity assays are known to one skilled in the art. One such assay is the CellTiter 96 non-radioactive cell proliferation/cytotoxicity assay available from Promega (Madison, Wis.) and described in Promega News, August 1991, pp. 1–4.

EXAMPLE 4

Creation of variant forms of 5HTT protein and testing for ligand binding and transport activity Comparison of 5HTT to other proteins indicates no significant homology except to NET and GAT-1. Hydropathicity plots are nearly superimposable for these three proteins. Overall, 5HTT has 41% identity to GAT-1 and 49% identity to NET at the amino acid level. Accounting for conservative substitutions, the levels of similarity increase to 62% and 65%, respectively. 5HTT is more similar to NET than to GAT-1, especially in the first eight transmembrane domains. The intracellular amino- and carboxy-tails are least conserved among these three transporters, thus alteration of this region provides for the study of diverse physiologic responses of the different transporters.

As expected, the region of the consensus oligonucleotide, constituting the outer half of transmembrane regions (TM) 1 and 2 with the connecting extracellular domain, is highly conserved among the three transporter proteins (FIG. 1). At the nucleotide level, 48 of 61 bases were identical. These results suggested that the probe might be useful for identifying additional members of this gene family; indeed, using this oligonucleotide, we have isolated a cDNA encoding the brain dopamine transporter (Usdin, T. et al, (in preparation)). The creation of chimeric molecules mixing domains from the 5HT transporter and the dopamine transporter will help elucidate the determinants of ligand binding.

Another region of possible functional significance is the conserved "leucine-zipper" motif in TM 2 with leucine or isoleucine repeating at seven residue intervals with interspersed prolines (FIG. 2) (Pacholczyk, T. et al., *Nature* 350, 350 (1991), White, M. K. and Weber, M. J. *Nature* 340, 103 (1989)). In GAT-1 and NET, this repeat is conserved, while in 5HTT, the interval between the second and third leucines is imperfect. It has been suggested that the leucine zipper may facilitate dimerization of glucose transporters (White, M. K. and Weber, M. J. *Nature* 340, 103 (1989)).

To assess the influence of the conserved leucine zipper motif on 5HTT function, one might mutate the leucine at residue 132 to an alanine residue. To accomplish this, the 5HTT cDNA is removed from the pCDM7 vector by cleavage of the recombinant DNA with XbaI and purification of the 5HTT cDNA insert by elution from an agarose gel after electrophoretic separation from the vector DNA. The 5HTT insert is then ligated into the pSELECT vector (Promega, Madison, Wis.) and site-directed mutagenesis of the desired nucleotides is accomplished using the ALTERED SITES kit (Promega, Madison, Wis.) and a mutagenic oligonucleotide of the sequence:

5'-CCTTATACCATCATGGCCATTTTCGGGGGGATCCCGCGCTTTTACATGGAGCTC-3' (SEQ. ID. NO. xx)

The mutant cDNA insert is then reisolated by separation of the XbaI fragments of the mutant pSELECT recombinant and recloned into a suitable mammalian cell expression vector, for instance, pCDNA1 (InVitrogen, San Diego, Calif.). The expression plasmid, containing the mutant DAT cDNA is then transfected into an appropriate host cell, such as CV-1 cells infected with a recombinant vaccinia virus expressing T7 polymerase (above). The thus transfected cells are then assayed for dopamine transporter activity using the uptake assay described above.

EXAMPLE 5

Creation of a permanent cell line expressing 5HTT at the cell surface.

The 5HTT cDNA cloned in the plasmid vector pCDM7 is useful as a means of constitutive expression of 5HTT protein in mammalian cells. CHO cells (other cell lines may be used as well) are transfected by $CaPO_4$ precipitation with equimolar amounts of pCDNEO as described in detail by Chen and Okayama (Chen, C. and Okayama, H., *Mol. Cell Biol.* 7, 2745 (1982)). Cotransfectants and cells stably integrating neomycin resistant clones are selected by growth for three weeks in the antibiotic G418 (200–600 µg/ml). At the end of four weeks, individual cells are isolated, colonies grown, and colonies assayed for 5HTT expression by the uptake assay described above.

EXAMPLE 6

Diagnosis of gene variants in the serotonin transporter locus by Southern blotting.

DNA isolated from white blood cells by standard protocols (e.g. Sambrook, J. et al. "Molecular Cloning, A Laboratory Manual", 2nd edition, pp 9.14–9.23, c 1989 by Cold Spring Harbor Laboratory Press, Cold Spring Harbor, N.Y.) is analyzed by Southern blots using a number of restriction enzymes for Restriction Fragment Length Polymorphisms (RFLPs) showing relatively high frequency of population variants, using the stringencies defined by conditions required to obtain specific hybridization of 5HTT cDNA to human genomic DNA. RFLPs in this locus can then be examined for their distribution in a sample of 20 normal and 20 subjects diagnosed with clinical depression, amphetamine abuse or a psychiatric affective disorder. Any restriction fragment length polymorphic forms of the gene found in higher abundance in populations diagnosed as clinically depressed, or as abusers of amphetamine or as having psychiatric affective disorders, compared to a normal, control population are checked by ascertainment in other populations.

EXAMPLE 7

Diagnosis of deficiency, mutant or overexpression of serotonin transporter by PCR mRNA obtained from tissue biopsy from a patient is subjected to quantitative reverse-transcript PCR (for example, see A. M. Wang, et al. PNAS USA 86:9717 (1989)) utilizing as primers oligonucleotides derived from the cDNA sequence of 5HTT. Use of the 5' 17-mer, 5'-CAGAACTTG-GCAGCAGT-3', bases 70 through 87 of SEQ. I.D. NO. 1, as the upstream primer and 5'-GGAGTATTGGGATCGAG- 3', the reverse complement of bases 2674 to 2690 of SEQ. I.D. NO. 1, as the downstream primer, allows examination of the character of the majority of the 5HTT mRNA. Variance in the expression level can be ascertained by comparison of product yield with a normal control. Abnormal mRNA structures can be diagnosed by observation of a product band of a length different from the normal control. Point mutants can be observed by use of primers and conditions appropriate for detection of the mismatch between the mutant and normal alleles. For example, the "reverse dot blot" procedure for screening the expression of several mutant alleles in a single experiment, has been described for the CFTR gene, mutants of which cause cystic fibrosis (Erlich, H. A., et al *Science* 252:1643 (1991).

EXAMPLE 8

A biosensor for the measurement of serotonin, amphetamine, MDMA or analogs thereof in physiologic samples.

Biosensors consisting of 5HTT protein or the ligand binding portions thereof and a piezoelectric crystal can be created and utilized for the measurement of 5HTT ligands in samples. The literature describing the use of ligand binding proteins as components in biosensors is large and expanding. Review of the art is given by Luong, et al. (Luong, J. H. T, et al. Trends Biotehnol. 6, 310–3316 (1988)) and Wingard (Wingrad, L. B. Jr. Ann. N.Y. Acad. Sci. 613, 44–53 (1990)), who discusses the applications of neuroreceptors to the art. Specific protocols for the attachment of proteins to piezoelectric crystals made be found in Davis and Leary (Davis, K. A. and Leary, T. R. Anal. Chem 61, 1227–1230 (1989)) or Guilbault, et al. (Guibault, G. G. et al. Bio/Technology 7, 349–351 (1989)).

EXAMPLE 9

Production of antibodies to 5HTT and use of same in a diagnostic test for serotonergic cell function.

A. Production of polyclonal antibodies to 5HTT.

5HTT protein obtained as described above or synthetic polypeptides of amino acid sequence derived from the 5HTT sequence are used as immunogens in an appropriate animal. The serum is obtained from the immunized animal and either utilized directly or the antibody may be purified from the serum by any commonly utilized techniques. Polyclonal antibody directed only toward 5HTT can be isolated by use of an affinity column derivatized with the immunogen utilized to raise the antibody, again using techniques familiar to one knowledgable in the art.

B. Production of monoclonal antibodies to 5HTT

Monoclonal antibodies to particular epitopes of 5HTT may be produced by immunization of an appropriate animal with 5HTT protein obtained as above or with peptides of amino acid sequence derived from the 5HTT amino acid sequence. Hybridoma cultures are then established from spleen cells as described by Jaffe and McMahon-Pratt (Jaffe, C. L. and MacMahon-Pratt, D. J. Immunol. 131, 1987–1993 (1983)). Alternatively, peripheral blood lymphocytes may be isolated and immortalized by transformation with Epstein-Barr virus. These cells produce monoclonal antibodies, but if desired, hybridomas can then be made from the transformed lymphocytes (Yamaguchi, H. et al. Proc. Natl. Acad. Sci. 84, 2416–2420 (1987)). Cell lines producing anti-5HTT antibodies are identified by commonly employed screening techniques. Monoclonal antibody is then purified by well known techniques from the supernatants of large-scale cultures of the antibody producing cells.

C. Diagnosis of serotonergic cell function by immunoassay of using anti-5HTT antibodies.

The amount of serotonin transporter present in the tissue to be examined can be assayed by use of standard immunoassay techniques. An example of such a procedure can be found in "Antibodies, A Laboratory Manual", by E Harlow and D Lane, c 1988 by Cold Spring Harbor Laboratory Press, Cold Spring Harbor, N.Y.

D. Conjugation of anti-5HTT antibodies to toxins, solid supports or labels.

Anti-5HTT antibodies coupled to a solid support, for example an agarose chromatography support, may find utility in protocols for the purification or assay of 5HTT protein. Conjugation to cytotoxins may prove useful, for example, for the selective ablation of cells expressing 5HTT. Labelling of the anti-5HTT antibodies with fluorescent, enzymatic or radioactive tags might provide useful reagents, for example, for immunohistochemistry assays. Such conjugations are all well-known to a practitioner skilled in the art.

EXAMPLE 10

Expression of 5HTT protein in *Escherichia coli* and purification of the bacterially expressed protein.

Any of several expression systems can be utilized to obtain 5HTT protein expression in *E. coli*. For example, the plasmid vector pFLAG system (International Biotechnologies, Inc., New Haven, Conn.) produces the polypeptide of interest attached to a short protein sequence that allows purification of the fusion protein by use of a monoclonal antibody directed against a hydrophilic, and thus probably surface localized, octapeptide. The the majority of the open reading frame portion of the 5HTT cDNA is obtained by EcoRI digestion and purification of the 2.4 kilobasepair fragment by electrophoresis and elution from an agarose gel by standard techniques and cloned into the Multiple Cloning Site of the pFLAG vector (International Biotechnologies, Inc.) in such a manner as to place the 5HTT cDNA in the correct orientation and reading frame as to produce a 5HTT fusion peptide. The appropriate *E. coli* host is transformed and colonies containing the 5HTT cDNA may be screened by colony hybridization using the 5HTT cDNA as probe. Positive clones are grown as large-scale cultures and the fusion protein is obtained in pure form by use of the monoclonal antibody affinity column as described by the manufacturer of the system. The protocol for the column purification may be modified as needed to obtain sufficient yield and purity by means apparent to one skilled in the art. Authentic 5HTT protein lacking the FLAG octapeptide is obtained by enterokinase cleavage of the fusion protein as described by the supplier of the FLAG system.

EXAMPLE 11

Purification of 5HTT from tissues or from transformed mammalian cells.

As protein isolated from transformed bacterial cells lacks post-translational modifications, such as sugar additions, that occur in mammalian cells, the purification of the protein from tranformed CHO cells is discussed.

A partial purification of the serotonin transporter protein has been reported by Biessen, et al. (Biessen, E. A. L. et al., Biochem. Soc. Trans. 19, 103–111 (1991)). CHO cells expressing the 5HTT cDNA, established as described above may be utilized as a source of the protein for partial purification by the technique described by Biessen et al. The protocol will be modified as required to allow the isolation of 5HTT as a distinct protein by techniques known to a practitioner of the art. Biessen et al. note that the probable molecular weight of the serotonin transporter polypeptide is approximately 78 kilodaltons as measured by SDS-PAGE.

Crude preparations of membrane fractions suitable for use in ligand binding experiments may be prepared as described in Teitler et al. (Teitler, M. et al, J. Neurochem., 38, 594–598 (1990)).

What is claimed is:

1. An isolated DNA molecule encoding a serotonin transporter protein consisting of a DNA molecule having a nucleotide sequence which encodes the amino acid sequence of SEQ. I.D. NO. 2.

2. An isolated DNA molecule of claim 1, wherein said nucleotide sequence is the nucleotide sequence of SEQ. I.D. NO. 1.

3. A recombinant DNA molecule comprising a nucleotide sequence encoding the amino acid sequence of SEQ. I.D. NO. 2. or conservatively modified variants thereof.

4. A recombinant DNA molecule comprising the nucleotide sequence of SEQ. I.D. NO. 1. or conservatively modified variants thereof.

5. A method for isolating a cDNA encoding a serotonin transporter protein, which comprises:

i) providing and apportioning a cDNA library of plasmids, wherein the complement of the messenger RNA of a cell type which expresses a serotonin transporter protein is represented as cDNA clones in a vector, wherein said vector directs transcription of said cDNA from a cytomegalovirus or T7 bacteriophage promoter;

ii) introducing at least one of said plasmids into a eukaryotic cell, wherein said cell is able to express said cDNA;

iii) culturing said cells containing said plasmids in a medium which contains radioactive serotonin;

iv) fixing the cells in acrolein and glutaraldehyde;

v) exposing the fixed cells to a photographic emulsion to identify cells which have sequestered the radiolabelled serotonin by transporting said radiolabelled serotonin into said cell from the medium; and vi) reiterating steps (i)–(v) until a specific plasmid is identified which confers serotonin transport activity upon said cells into which it is introduced.

* * * * *